US010836783B2

(12) United States Patent
Tanaka et al.

(10) Patent No.: US 10,836,783 B2
(45) Date of Patent: *Nov. 17, 2020

(54) INCLUSION COMPOUND OF 3',5'-CYCLIC DIADENYLIC ACID AND MANUFACTURING METHOD THEREOF

(71) Applicant: Yamasa Corporation, Choshi (JP)

(72) Inventors: Hisaki Tanaka, Choshi (JP); Kazuya Ishige, Choshi (JP)

(73) Assignee: Yamasa Corporation, Choshi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 16/451,673

(22) Filed: Jun. 25, 2019

(65) Prior Publication Data
US 2019/0382426 A1    Dec. 19, 2019

Related U.S. Application Data

(62) Division of application No. 15/125,349, filed as application No. PCT/JP2015/057386 on Mar. 12, 2015, now abandoned.

(30) Foreign Application Priority Data

Mar. 14, 2014 (JP) ................ 2014-052076
Nov. 21, 2014 (JP) ................ 2014-236800

(51) Int. Cl.
| C07F 9/6561 | (2006.01) |
| C07H 1/00 | (2006.01) |
| C07H 21/02 | (2006.01) |

(52) U.S. Cl.
CPC .......... *C07F 9/6561* (2013.01); *C07H 1/00* (2013.01); *C07H 21/02* (2013.01)

(58) Field of Classification Search
CPC .......... C07H 1/00; C07H 21/02; C07F 9/6561
USPC ..................... 536/26.12; 544/244
See application file for complete search history.

(56) References Cited

U.S. PATENT DOCUMENTS

| 2006/0167241 A1 | 7/2006 | Hayakawa |
| 2008/0286296 A1 | 11/2008 | Ebensen et al. |
| 2009/0169609 A1 | 7/2009 | Ebensen et al. |
| 2012/0040403 A1 | 2/2012 | Liang et al. |
| 2012/0164107 A1 | 6/2012 | Portnoy et al. |
| 2015/0044724 A1 | 2/2015 | Tanabe et al. |
| 2017/0096439 A1 | 4/2017 | Tanaka et al. |
| 2017/0101432 A1 | 4/2017 | Tanaka et al. |

FOREIGN PATENT DOCUMENTS

| CN | 102199183 A | 9/2011 |
| EP | 1645561 A1 | 4/2006 |
| WO | WO-2007/054279 A2 | 5/2007 |
| WO | WO 2010/101526 A1 * | 9/2010 | .......... C07H 19/213 |
| WO | WO-2013/129427 A1 | 9/2013 |

OTHER PUBLICATIONS

Frederick et al, Biochemistry, 1988, 27, 8350-61.*
Caira, Topics in Current Chemistry, 1998, 198, 163-208.*
Amiot et al., "New approach for the synthesis of c-di-GMP and its analogues," Synthesis. 24:4230-6 (2006).
Ault, Separation of Substances, *Techniques and Experiments for Organic Chemistry: Fifth Edition.* Waveland Press, Inc., 44-54 (1987).
Extended European Search Report for European Patent Application No. 15761774.7 dated Dec. 21, 2016, Tanaka et al., "Inclusion Compound of 3',5'-cyclicdiadenylic acid, and method for producing same," filed Jan. 1, 2017 (8 pages).
Frederick et al., "Molecular structure of cyclic deoxydiadenylic acid at atomic resolution," Biochemistry. 27(22):8350-61 (1988).
Gaffney et al., "Synthesis of biotinylated c-di-gmp and c-di-amp using click conjugation," Nucleosides Nucleotides Nucleic Acids. 32(1):1-16 (2013).
International Search Report for International Patent Application No. PCT/JP2015/057386, dated Apr. 7, 2015 (7 pages).
Kamegaya et al., "Identification of a *Streptococcus pyogenes* SF370 gene involved in production of c-di-AMP," Nagoya J Med Sci. 73(1-2):49-57 (2011).
Ohtsuka et al., "Studies on transfer ribonucleic acids and related compounds. VII. Synthesis and properties of cyclic oligoadenylic acids," Chem Pharm Bull. 22(5):1022-8 (1974).
Witte et al., "Structural biochemistry of a bacterial checkpoint protein reveals diadenylate cyclase activity regulated by DNA recombination intermediates," Mol Cell. 30(2):167-78 (2008).
Woodward et al., "c-di-AMP secreted by intracellular Listeria monocytogenes activates a host type I interferon response," Science. 328(5986):1703-5 (2010).
Caira et al., "Crystalline polymorphism of organic compounds," Topics in Current Chemistry. 198:163-208 (1998).
Chen et al., "The potential of 3',5'-cyclic diguanylic acid (c-di-GMP) as an effective vaccine adjuvant," Vaccine. 28(18):3080-5 (2010).
Egli et al., "Atomic-resolution structure of the cellulose synthase regulator cyclic diguanylic acid," Proc Natl Acad Sci USA. 87(8):3235-9 (1990).
Extended European Search Report dated Jan. 25, 2017 for European Patent Application No. 15759144.7, Tanaka et al., "Crystalline 3',5'-cyclic Diguanylic Acid," filed Feb. 27, 2015 (10 pages).
Gaffney et al., "One-flask syntheses of c-di-GMP and the [Rp,Rp] and [Rp,Sp] thiophosphate analogues," available in PMC Jul. 16, 2011, published in final edited form as: Org Lett. 12(14):3269-71 (2010) (5 pages).
Guan et al., "Molecular structure of cyclic diguanylic acid at 1 A resolution of two crystal forms: self-association, interactions with metal ion/planar dyes and modeling studies," J Biomol Struct Dyn. 11(2):253-76 (1993).

(Continued)

*Primary Examiner* — Ganapathy Krishnan
(74) *Attorney, Agent, or Firm* — Clark & Elbing LLP; Susan M. Michaud

(57) ABSTRACT

Though 3',5'-cyclic diadenylic acid was conventionally provided only as a freeze-dried product, a solid material other than a freeze-dried product and a manufacturing method thereof is provided. By a step of adding acid to an aqueous solution of 3',5'-cyclic diadenylic acid so as to lower pH to 1 to 3, an inclusion compound of 3',5'-cyclic diadenylic acid can be obtained. Said manufacturing method is an extremely simple and easy method and does not need a special machine or the like.

4 Claims, 14 Drawing Sheets

(56) References Cited

OTHER PUBLICATIONS

Hirayama, Yuki Kagobutsu Kessho Sakusei Handbook, pp. 17-23, 37-40, 45-51, 57-65 (2008) (44 pages).
International Search Report for International Patent Application No. PCT/JP2015/055975, dated Apr. 21, 2015 (5 pages).
Ishige, Bioscience & Industry. 70(6):466-7, Nov. 1, 2012 (4 pages).
Karaolis et al., "c-di-GMP (3'-5'-cyclic diguanylic acid) inhibits *Staphylococcus aureus* cell-cell interactions and biofilm formation," Antimicrob Agents Chemother. 49(3):1029-38 (2005).
Liaw et al., "Cyclic diguanylic acid behaves as a host molecule for planar intercalators," FEBS Lett. 264(2):223-7 (1990).
Office Action dated Apr. 6, 2018 for Korean Application No. 10-2016-7025780, Tanaka et al., "3'5'-crystalline 3'5'-cyclic diguanylic acid," filed Feb. 27, 2015 (9 pages).
Office Action dated Apr. 8, 2019 for Chinese Patent Application No. 201580010888.X, Tanaka et al., "Crystalline 3',5'-cyclic Diguanylic Acid," filed Feb. 27, 2015 (14 pages).
Office Action dated Sep. 18, 2017 for Canadian Application No. 2,941,353, Tanaka et al., "Crystalline 3',5'-Cyclic Diguanyic Acid," filed Feb. 27, 2015 (6 pages).
Office Action dated Sep. 30, 2018 for Chinese Patent Application No. 201580010888.X, Tanaka et al., "Crystalline 3',5'-cyclic Diguanylic Acid," filed Feb. 27, 2015 (11 pages).
Written Opinion for International Patent Application No. PCT/JP2015/055975, dated Apr. 21, 2015 (7 pages).
Xiao, Principles of Microbial Engineering, China Light Industry Press, 292-8 (2004) (8 pages).
Yan et al., "Synthesis of 3',5'-cyclic diguanylic acid (cdiGMP) using 1-(4-chlorophenyl)-4-ethoxypiperidin-4-yl as a protecting group for 2'-hydroxy functions of ribonucleosides," Nucleosides, Nucleotides, and Nucleic Acids. 26(2):189-204 (2007).
Zhang et al., "c-di-GMP displays a monovalent metal ion-dependent polymorphism," J Am Chem Soc. 126(51):16700-1 (2004).
Takata, "Soyaku Dankai ni Okeru Gen'yaku Form Screening to Sentaku: API form screening and selection in drug discovery stage," Pharm Stage. 6(10):20-5 (2007) (19 pages).

* cited by examiner

INCLUSION COMPOUND OF 3',5'-CYCLIC DIADENYLIC ACID AND MANUFACTURING METHOD THEREOF

TECHNICAL FIELD

The present invention is related to an inclusion compound of 3',5'-cyclic diadenylic acid, which is deemed to be a useful substance as an adjuvant, and a manufacturing method thereof.

BACKGROUND

3',5'-Cyclic diadenylic acid is a substance discovered as a second messenger of bacteria. Recently, an application as a pharmaceutical is expected since, for example, said substance is reported to be capable of inducing type 1 interferon (Non-Patent Document 1).

As a manufacturing method of 3',5'-cyclic diadenylic acid, a chemical synthesis method (Non-Patent Documents 2 and 3) and an enzymatic synthesis method (Non-Patent Documents 4 and 5), in which diguanylate cyclase from Genus *Bacillus*, Genus *Streptococcus* or the like is used, are known thus far, and it is provided in the form of a freeze-dried product.

PRIOR ART DOCUMENTS

Non-Patent Documents

Non-Patent Document 1: Science, 328, 1703-1705(2010)
Non-Patent Document 2: SYNTHESIS, 24, 4230-4236 (2006)
Non-Patent Document 3: Nucleosides Nucleotides Nucleic Acids, 32, 1-16(2013)
Non-Patent Document 4: Molecular Cell, 30, 167-178(2008)
Non-Patent Document 5: Nagoya J. Med. Sci., 73, 49-57 (2011)

SUMMARY

Problems to be Solved by the Invention

Though 3',5'-cyclic diadenylic acid is provided conventionally as a freeze-dried product, no preparation other than the freeze-dried product has been known. However, a freeze-dried product requires a freeze dryer in the manufacturing process thereof, so that even if scaling up is intended for mass production, limitations inevitably exist.

Therefore, an object of the present invention is to provide a completely novel preparation of 3',5'-cyclic diadenylic acid that is different from a freeze-dried product, without using a special apparatus nor step.

Means to Solve the Problems

The present inventors studied preparations of 3',5'-cyclic diadenylic acid different from a freeze-dried product. As a result, it was newly found that by a extremely simple and easy method of adding acid to an aqueous solution of 3',5'-cyclic diadenylic acid so as to lower pH to 1 to 3, an inclusion compound of 3',5'-cyclic diadenylic acid can be manufactured that has physical properties completely different from those of a freeze-dried product.

Advantageous Effect of the Invention

The present invention provides an inclusion compound of 3',5'-cyclic diadenylic acid that is completely different from the conventional freeze-dried product. The inclusion compound of the present invention is a crystalline substance, and thus, easy to handle (for example, free from hygroscopicity, excellent in stability and solubility, and the like). Further, the manufacturing method of the inclusion compound of 3',5'-cyclic diadenylic acid of the present invention does not need a special apparatus nor step for preparing, and is useful in producing 3',5'-cyclic diadenylic acid in large amount.

DETAILED DESCRIPTION OF PREFERRED EMBODIMENTS

Figure 1:
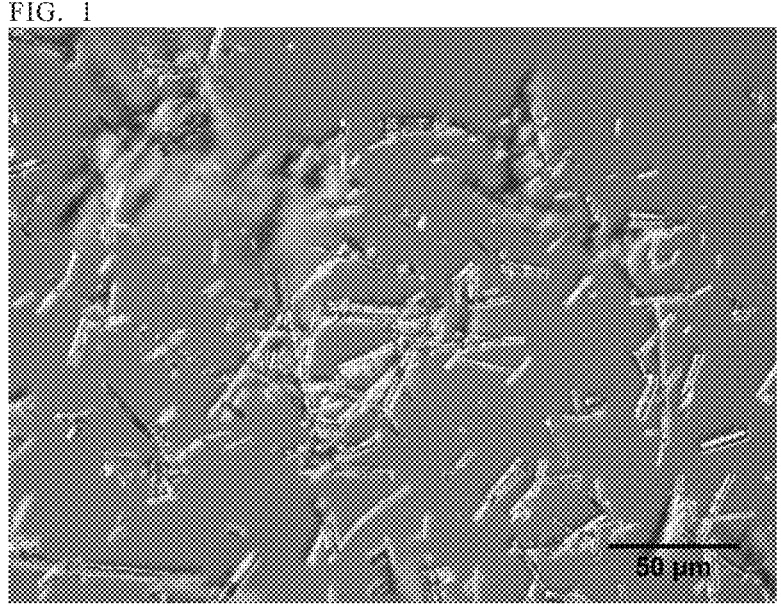
FIG. 1 shows a photograph of an inclusion compound (amorphous) of 3',5'-cyclic diadenylic acid.

The present invention provides an inclusion compound of 3',5'-cyclic diadenylic acid represented by the following structural formula.

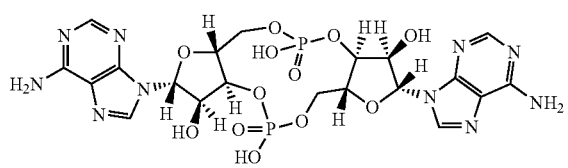 [SMILES: Nc1ncnc2c1ncn2[C@@H]1O[C@@H]2COP(=O)(O)O[C@H]3[C@@H](O)[C@H](n4cnc5c(N)ncnc54)O[C@@H]3COP(=O)(O)O[C@H]2[C@H]1O]

The inclusion compound referred to in this invention means a solid material in a state where a solvent plays an auxiliary role in solidification, such that the compound and the solvent form a complex by weak interactions, and the configuration of inclusion and the structure of solidification are not limited. In particular, in the present invention, since water is used as the solvent, the inclusion compound in the present invention means an inclusion compound with water. Note that the inclusion compound of the present invention encompasses a crystalline substance and an amorphous substance.

The inclusion compound of 3',5'-cyclic diadenylic acid of the present invention can be obtained by adding acid to an aqueous solution of 3',5'-cyclic diadenylic acid so as to lower pH to 1 to 3.

3',5'-Cyclic diadenylic acid used to obtain the inclusion compound of the present invention may be synthesized by a known method such as the enzymatic synthesis method and the chemical synthesis method, and one synthesized by the enzymatic synthesis method is preferable. Enzymatic synthesis may be performed following the known method and, for example, the method described in Patent Documents 4 and 5 may be used. After the reaction, 3',5'-cyclic diadenylic acid generated in a reaction solution can be isolated and purified by the usual chromatography method using activated carbon, an ion-exchange resin or the like.

In order to obtain the inclusion compound of the present invention, acid may be added to an aqueous solution of 3',5'-cyclic diadenylic acid so as to lower pH to 1 to 3, preferably to 1.5 to 2.0. The acid used may be any one that can regulate pH into the range mentioned above, and specifically, inorganic acids such as hydrochloric acid, sulfuric acid and nitric acid can be exemplified. Note that in order to prevent amorphism or rapid precipitation from being caused by adding acid rapidly, slow addition is preferable.

Further, if a yield of the inclusion compound is low, the inclusion compound may be obtained again by performing said process repeatedly several times on the filtrate of said inclusion compound.

Further, in obtaining the inclusion compound of the present invention, a method may be employed which comprises (1) a step of adding acid to an aqueous solution of 3',5'-cyclic diadenylic acid so as to lower pH to 1 to 3, (2) a step of heating said aqueous solution of 3',5'-cyclic diadenylic acid to 50 to 70° C., and (3) a step of cooling said aqueous solution of 3',5'-cyclic diadenylic acid until the solution reaches 1 to 10° C. Further, steps (1) and (2) or steps (2) and (3) may be performed simultaneously. Moreover, a method may be employed which consists of (1) a step of adding acid to a diluted aqueous solution of 3',5'-cyclic diadenylic acid so as to lower pH to 1 to 3, (2) a step of heating said aqueous solution of 3',5'-cyclic diadenylic acid with adjusted pH to 50 to 70° C., and (3) a step of cooling said aqueous solution of 3',5'-cyclic diadenylic acid until the solution reaches 1 to 10° C. In order to obtain the inclusion compound certainly, it is preferable that cooling in step (3) is performed slowly. Specifically, cooling with a temperature gradient of −3 to −11° C./hr is preferable.

The inclusion compound of 3',5'-cyclic diadenylic acid obtained by the manufacturing method described above may be collected by filtration and then dried at a room temperature (25° C.) to 70° C. for 1 to 10 hours, to be a product. The inclusion compound of the present invention can be obtained as a crystalline substance by drying at a low temperature ranging from a room temperature (25° C.) to 40° C., and as an amorphous substance by drying under a high temperature condition ranging from 40 to 70° C. Specifically, the inclusion compound of the present invention is obtained as a crystalline substance by drying at a low temperature of a room temperature (25° C.) or higher and lower than 40° C., and as an amorphous substance by drying under a high temperature condition of 40° C. or higher and 70° C. or lower. Further, the inclusion compound obtained may be washed as appropriate with ethanol or the like after collecting by filtration and before drying. A method of drying under reduced pressure may be utilized as appropriate in drying.

The inclusion compound of 3',5'-cyclic diadenylic acid of the present invention obtained by the method described above has purity of 97% or more, preferably 99% or more, when purity test is performed by the high performance liquid chromatography method, as well as the following physical properties. Note that among the physical properties below, those not specifically limited are common to both the crystalline substance and the amorphous substance.

(1) Water Content

The inclusion compound of 3',5'-cyclic diadenylic acid of the present invention has water content of 3.5 to 17% as measured by a thermogravimetric measurement/differential thermal analysis (TG/DTA) apparatus, though it varies according to the extent of drying. That is, in the inclusion compound of 3',5'-cyclic diadenylic acid of the present invention, 1 to 7 molecules of water, more specifically, 1.1 to 6.1 molecules of water bond or attach to one molecule of 3',5'-cyclic diadenylic acid.

(2) Thermal Analysis

When analyzed by a thermogravimetric measurement/differential thermal analysis (TG/DTA) apparatus (temperature elevation rate of 5° C./min), the inclusion compound of 3',5'-cyclic diadenylic acid of the present invention has an endothermic peak around 193° C. when the inclusion compound is a crystalline substance and around 220° C. when the inclusion compound is an amorphous substance.

(3) Shape

The inclusion compound of 3',5'-cyclic diadenylic acid of the present invention is needle-shaped.

(4) Infrared Absorption Spectrometry

The inclusion compound (amorphous) of 3',5'-cyclic diadenylic acid of the present invention has characteristic peaks around 3087, 1686, 1604, 1504, 1473, 1415, 1328 and 1213 ($cm^{-1}$) when an infrared absorption spectrum is measured.

Note that generally an error range less than 2 ($cm^{-1}$) is sometimes included in measuring an infrared absorption spectrum, so that not only inclusion compounds whose peak positions in an infrared absorption spectrum coincide exactly with the values noted above but also inclusion compounds whose peak positions coincide within the error range less than 2 $cm^{-1}$ are included in the inclusion compound of 3',5'-cyclic diadenylic acid of the present invention. For example, when an infrared absorption spectrum is measured, characteristic peaks are observed at 3087±1.9, 1686±1.9, 1604±1.9, 1504±1.9, 1473±1.9, 1415±1.9, 1328±1.9 and 1213±1.9 ($cm^{-1}$).

(5) X-Ray Powder Analysis

Especially in the case where the inclusion compound of 3',5'-cyclic diadenylic acid of the present invention is a crystalline substance, the inclusion compound of the present invention has characteristic peaks in X-ray powder analysis. For example, when the inclusion compound of the present invention is analyzed by an X-ray powder diffractometer using the Cu-Kα ray, characteristic peaks are observed, as shown in Example below, around 9.2, 10.2, 10.9, 11.1, 13.7, 15.2, 19.0, 20.6, 22.4, 23.1, 24.3, 26.6 and 26.8 (°) in diffraction angle (2θ), especially around 9.2, 15.2, 19.0, 20.6 and 26.8 (°) in diffraction angle (2θ)

Note that generally an error range less than 5% is sometimes included in diffraction angle (2θ) of X-ray powder diffraction, so that not only inclusion compounds whose diffraction angles of peaks in X-ray powder diffraction coincide exactly but also inclusion compounds whose diffraction angles of peaks coincide within the error range less than 5% are included in the inclusion compound of 3',5'-cyclic diadenylic acid of the present invention. For example, in X-ray powder diffraction, characteristic peaks are observed at 9.2±0.45, 10.2±0.50, 10.9±0.54, 11.1±0.55, 13.7±0.68, 15.2±0.75, 19.0±0.94, 20.6±1.02, 22.4±1.11, 23.1±1.15, 24.3±1.21, 26.6±1.32 and 26.8±1.33 (°) in diffraction angle (2θ), especially at 9.2±0.45, 15.2±0.75, 19.0±0.94, 20.6±1.02 and 26.8±1.33 (°) in diffraction angle (2θ).

In the case that the inclusion compound is an amorphous substance, no apparent peaks are observed in X-ray powder diffraction.

EXAMPLES

Hereafter, examples will be shown to explain the present invention specifically, however, it is apparent that the present invention is not limited thereto.

(Example 1) Manufacture of Inclusion Compound (Amorphous) of 3',5'-Cyclic Diadenylic Acid 3',5'-Cyclic diadenylic acid was synthesized and purified according to a known method.

A solution (141 mL) of 3',5'-cyclic diadenylic acid obtained by purification, with OD257 of 709, was diluted with water such that OD257 became 20. 1 N hydrochloric acid was added slowly with stirring to adjust pH to 1.8. As a result, white solids precipitated in the aqueous solution.

In order to obtain the inclusion compound more efficiently, said solution was warmed to 60° C. using a programmable incubator. Thereafter, the solution was cooled with a temperature gradient of −4° C./hr until the temperature of the solution reached 4° C. Precipitates were collected by a glass filter (17G3) to obtain white solids. Said white solids were dried at 60° C. for 6 hours and 2.169 g of inclusion compound (amorphous) was obtained.

(Reference Example) Manufacture of Freeze-Dried Product of 3',5'-Cyclic Diadenylic Acid After suspending 1 g of enzymatically synthesized 3',5'-cyclic diadenylic acid in 20 mL of water, pH was adjusted to 7.0 with 1 N NaOH or to 7.4 with 5% aqueous ammonia solution to dissolve the suspended 3',5'-cyclic diadenylic acid.

The solution in which 3',5'-cyclic diadenylic acid was dissolved was further diluted with water to 35 mL, and then, freeze-dried by a freeze dryer, thereby a freeze-dried product of sodium salt or ammonium salt of 3',5'-cyclic diadenylic acid was obtained.

(Example 2) Physical Properties of Inclusion Compound (Amorphous) of 3',5'-Cyclic Diadenylic Acid Instrumental analyses were performed on the inclusion compound of 3',5'-cyclic diadenylic acid prepared in Example 1 above, whose results are shown below.

(Instrumental Analysis)
(A) Purity Test

Purity of the inclusion compound of 3',5'-cyclic diadenylic acid obtained in Example 1 above was analyzed by the high performance liquid chromatography method. As a result, purity of 3',5'-cyclic diadenylic acid was 99.8%. Note that the high performance liquid chromatography method was performed under the following condition.
(Condition)
Column: Hydrosphere C18 (product of YMC Co., Ltd.)
Eluate: 0.1M TEA-P (pH 6.0)
Detection method: detection by UV 260 nm
(B) Shape A representative photograph of the inclusion compound of 3',5'-cyclic diadenylic acid is shown in FIG. 1. As seen from FIG. 1, it was revealed that the inclusion compound of 3',5'-cyclic diadenylic acid is needle-shaped.

Figure 2:
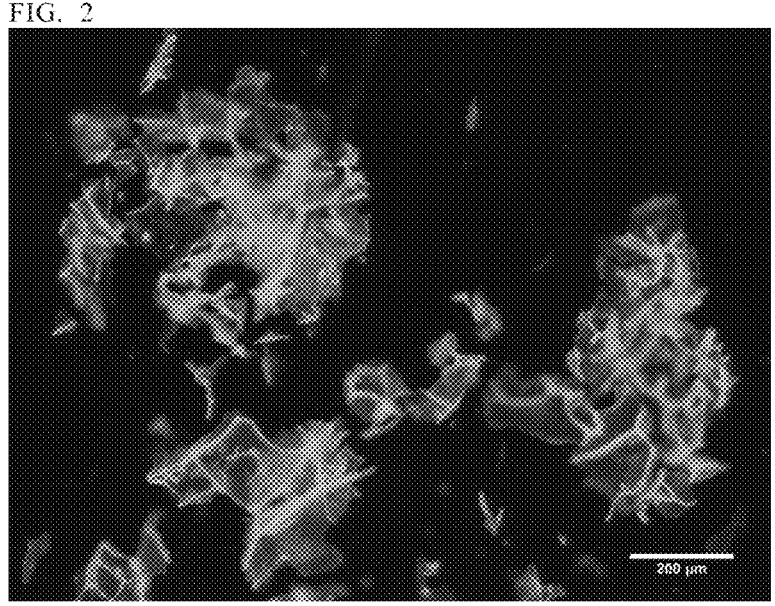
FIG. 2 shows a photograph of a freeze-dried product of sodium salt of 3',5'-cyclic diadenylic acid.
Figure 3:
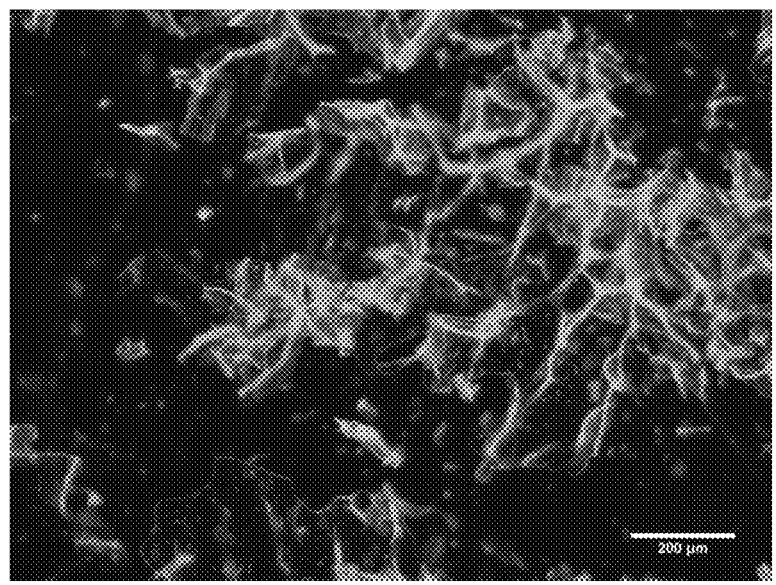
FIG. 3 shows a photograph of a freeze-dried product of ammonium salt of 3',5'-cyclic diadenylic acid.

Further, freeze-dried products of sodium salt of 3',5'-cyclic diadenylic acid and ammonium salt of 3',5'-cyclic diadenylic acid had, as shown in FIGS. 2 and 3, completely different shapes from that of the inclusion compound.
(C) Water Content When analyzed by a thermogravimetric measurement/differential thermal analysis (TG/DTA) apparatus (temperature elevation rate of 5° C./min), water content of the inclusion compound of 3',5'-cyclic diadenylic acid of the present invention was 8.7 to 9.5% for the inclusion compound before redrying, 3.5 to 3.6% for the inclusion compound after redrying at 100° C. under reduced pressure, 10.3% for the inclusion compound after redrying and subsequent storing at a room temperature and at a humidity of 40 to 50% overnight, 15.0% for the inclusion compound after redrying and subsequent storing at a temperature of 30° C. and at a humidity of 70% overnight, and 17.0% for the inclusion compound after vacuum dried at 20° C. for 2 hours.

That is, it was revealed from calculation that in the inclusion compound of 3',5'-cyclic diadenylic acid of the present invention, 1.1 to 6.1 molecules of water bond or attach to one molecule of 3',5'-cyclic diadenylic acid according to the extent of drying.

Figure 4:
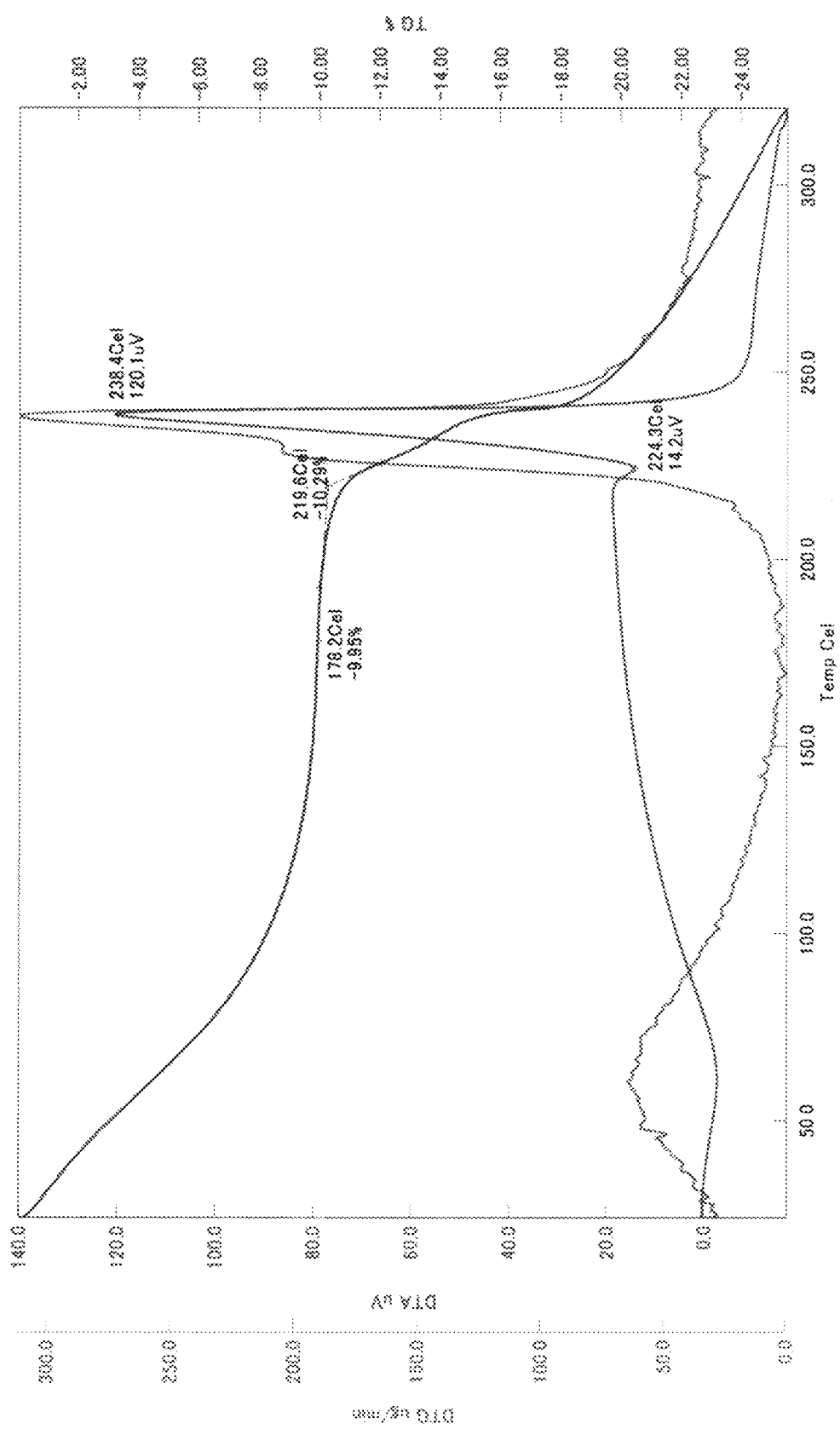
FIG. 4 shows a result of thermogravimetric measurement/differential thermal analysis of an inclusion compound (amorphous) of 3',5'-cyclic diadenylic acid.

Note that when thermogravimetric measurement was performed similarly on the freeze-dried product of sodium salt of 3',5'-cyclic diadenylic acid and on the freeze-dried product of ammonium salt of 3',5'-cyclic diadenylic acid, the freeze-dried product of sodium salt contained 16 to 17% of water and the freeze-dried product of ammonium salt contained 13 to 15% of water as their measured values before redrying.
(D) Differential Scanning Calorimetry When analyzed by a thermogravimetric measurement/differential thermal analysis (TG/DTA) apparatus (temperature elevation rate of 5° C./min), the inclusion compound of 3',5'-cyclic diadenylic acid of the present invention showed a characteristic endothermic peak around 220° C. (FIG. 4).

Figure 5:
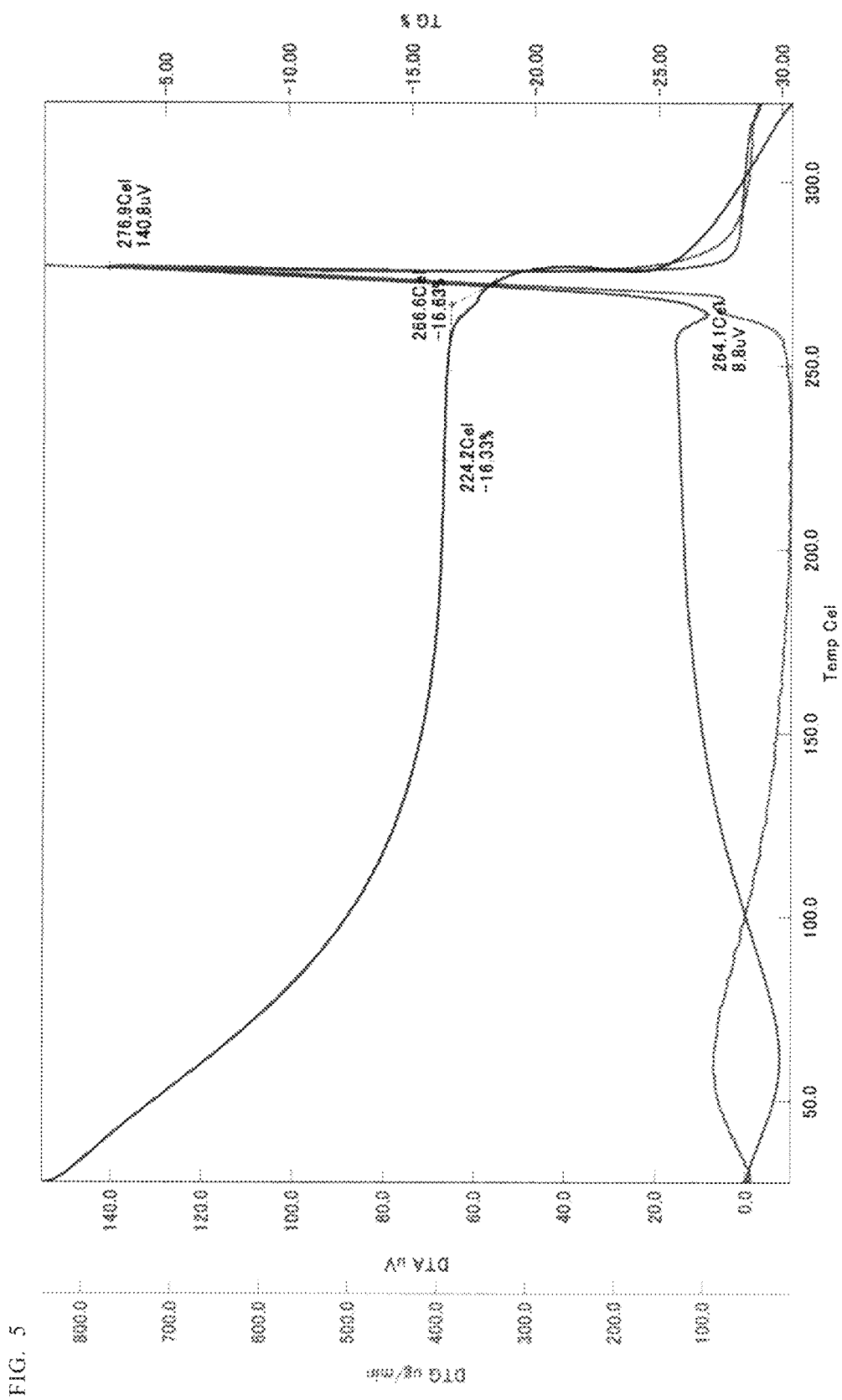
FIG. 5 shows a result of thermogravimetric measurement/differential thermal analysis of a freeze-dried product of sodium salt of 3',5'-cyclic diadenylic acid.
Figure 6:
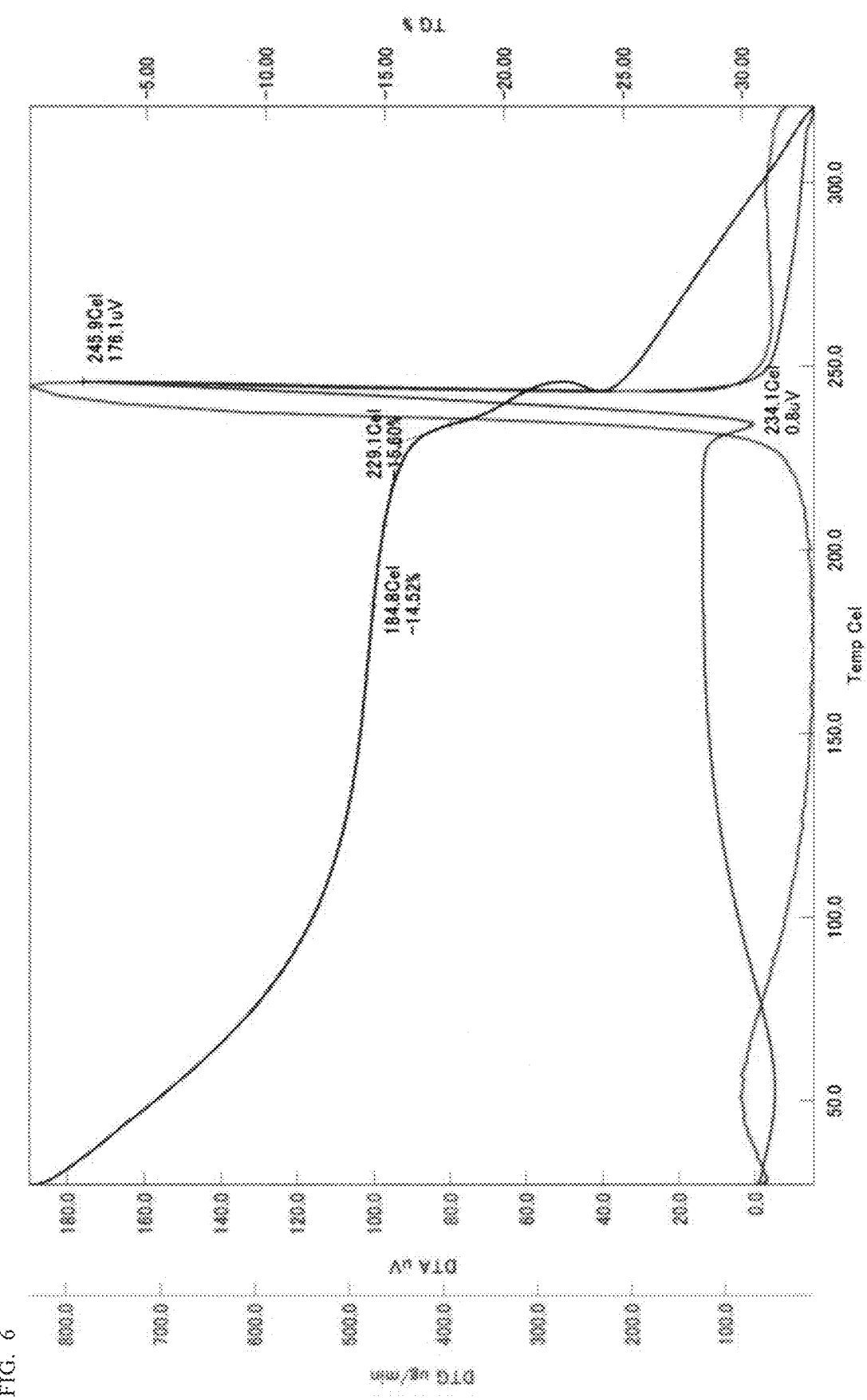
FIG. 6 shows a result of thermogravimetric measurement/differential thermal analysis of a freeze-dried product of ammonium salt of 3',5'-cyclic diadenylic acid.
Figure 7:
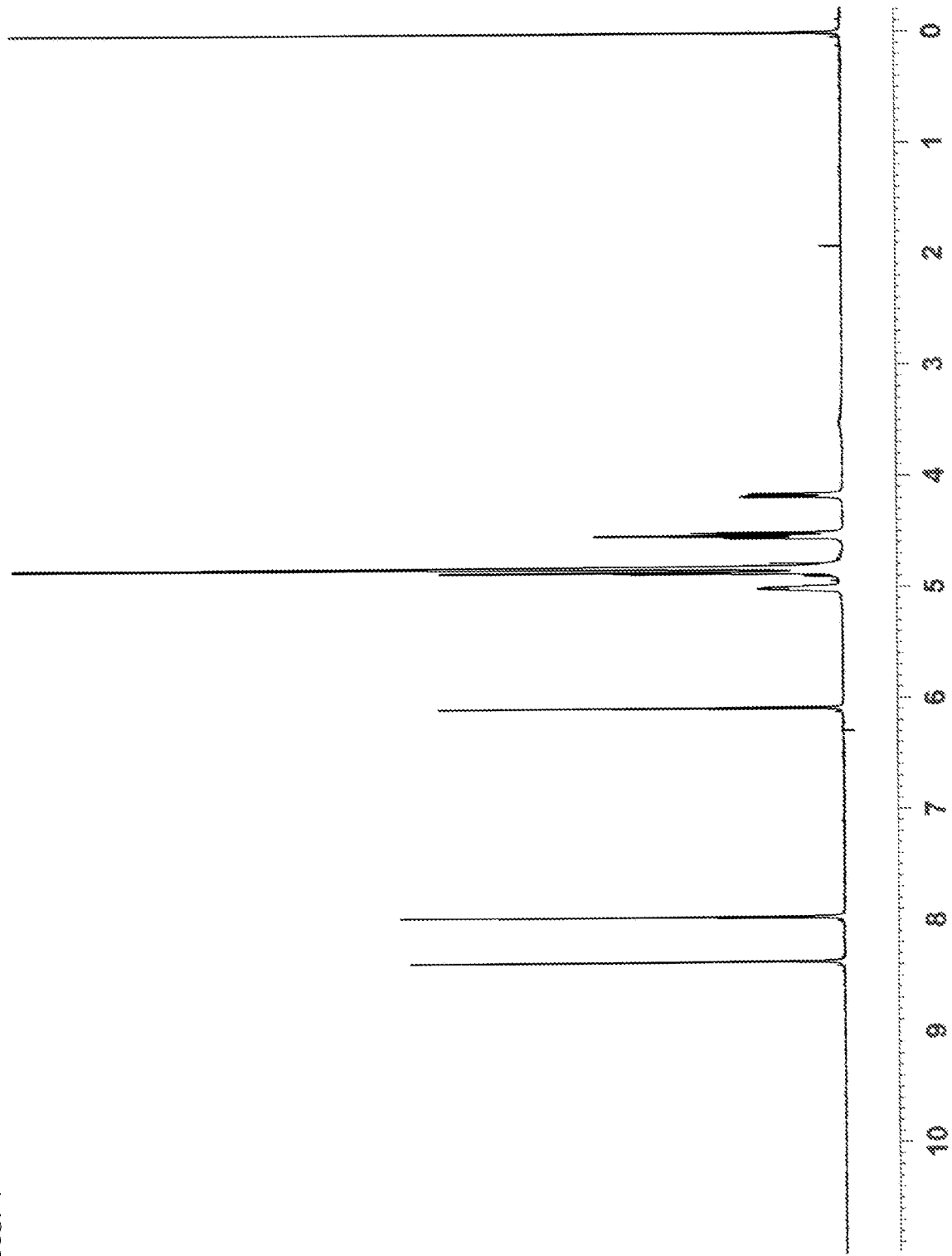
FIG. 7 shows a nuclear magnetic resonance spectrum ($^1$H) of an inclusion compound of 3',5'-cyclic diadenylic acid.
Figure 8:
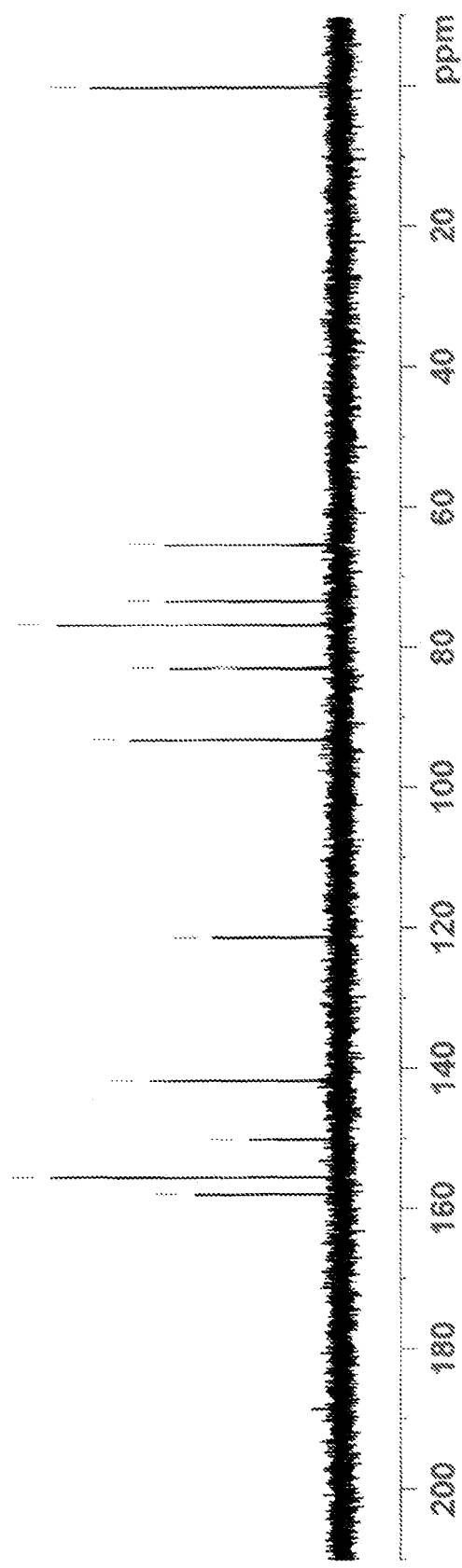
FIG. 8 shows a nuclear magnetic resonance spectrum ($^{13}$C) of an inclusion compound of 3',5'-cyclic diadenylic acid.
Figure 9:
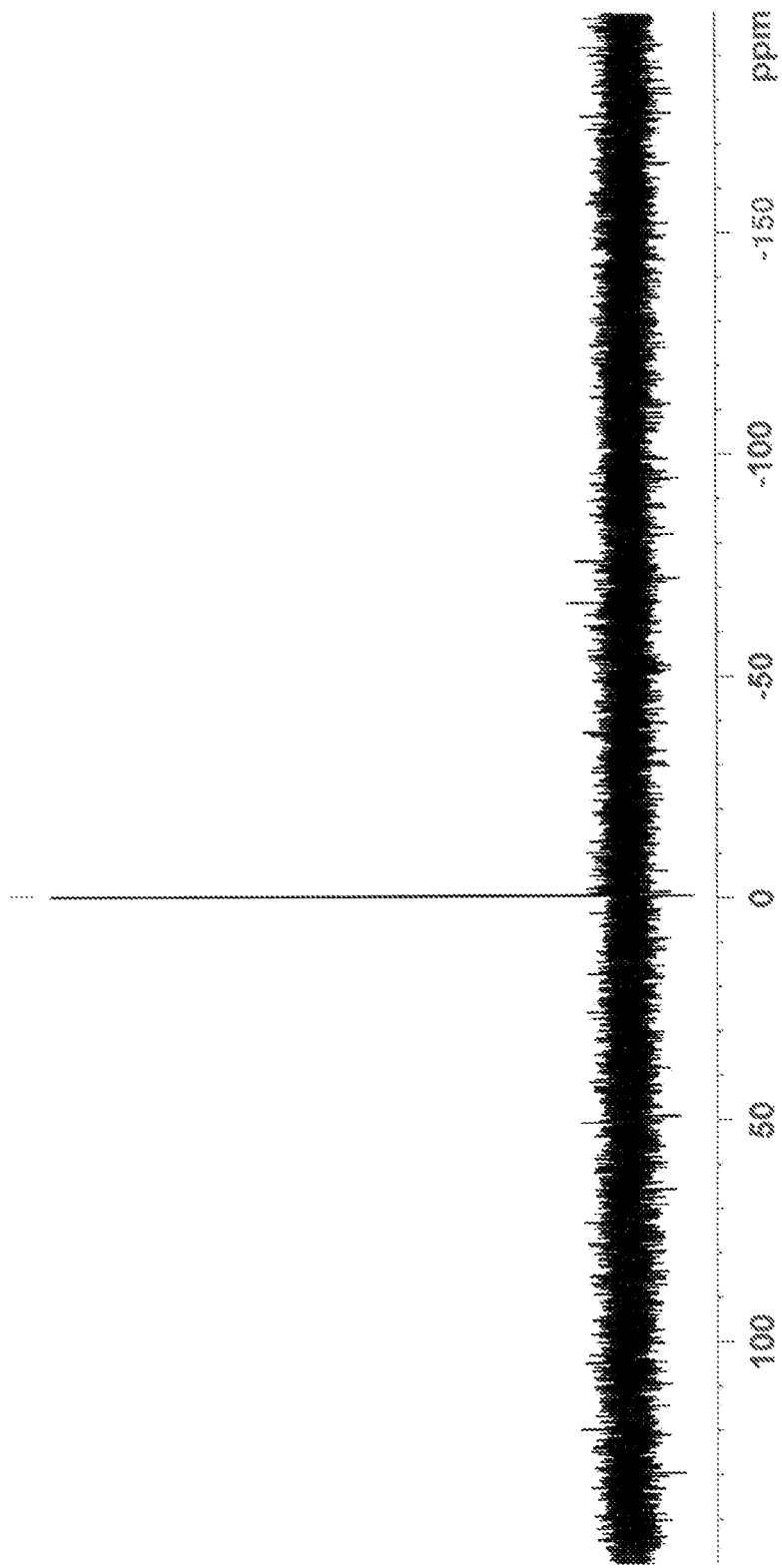
FIG. 9 shows a nuclear magnetic resonance spectrum ($^{31}$P) of an inclusion compound of 3',5'-cyclic diadenylic acid.

In contrast, the freeze-dried product of sodium salt of 3',5'-cyclic diadenylic acid showed an endothermic peak around 267° C. (FIG. 5) and the freeze-dried product of ammonium salt showed an endothermic peak around 228 to 229° C. (FIG. 6).
(E) Nuclear Magnetic Resonance Spectroscopy 2 μL of 6 N solution of NaOH was added to the inclusion compound of 3',5'-cyclic diadenylic acid of the present invention to dissolve it, which was diluted with heavy water to reach a concentration of 6 mg/0.6 mL, and nuclear magnetic resonance spectrum measurement ($^1$H, $^{13}$C, $^{31}$P) was performed. Results of the measurement are shown in FIGS. 7 to 9, respectively.

As a result, as for $^1$H, the inclusion compound of 3',5'-cyclic diadenylic acid of the present invention showed peaks around 8.37, 7.96, 6.08, 4.98-5.02, 4.86, 4.51-4.55 and 4.17 (ppm). Further, as for $^{13}$C, peaks were observed around 157.9, 155.4, 150.0, 141.6, 121.3, 93.1, 82.8, 76.7, 73.3 and 65.2 (ppm). As for $^{31}$P, a peak was observed around −0.91 (ppm).

(F) Infrared Absorption Spectrometry

Infrared absorption spectrum was measured on each of the inclusion compound of 3',5'-cyclic diadenylic acid of the present invention, and the freeze-dried product of sodium salt of 3',5'-cyclic diadenylic acid and the freeze-dried product of ammonium salt of 3',5'-cyclic diadenylic acid using a Fourier transform infrared spectrophotometer, Spectrum One (product of PerkinElmer Co., Ltd.) by the ATR (Attenuated Total Reflectance) method.

Figure 10:
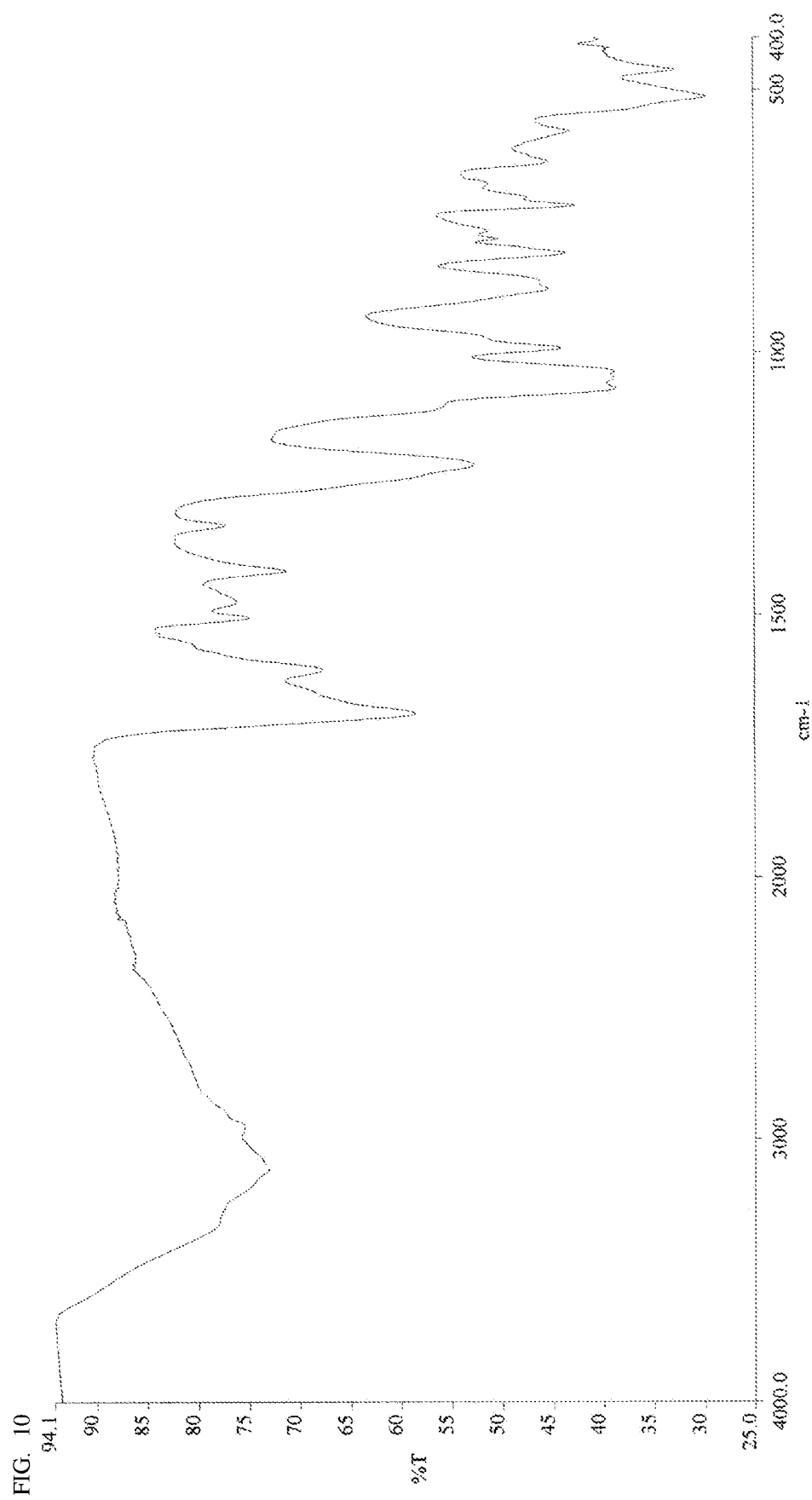
FIG. 10 shows an infrared absorption spectrum of an inclusion compound of 3',5'-cyclic diadenylic acid.
Figure 11:
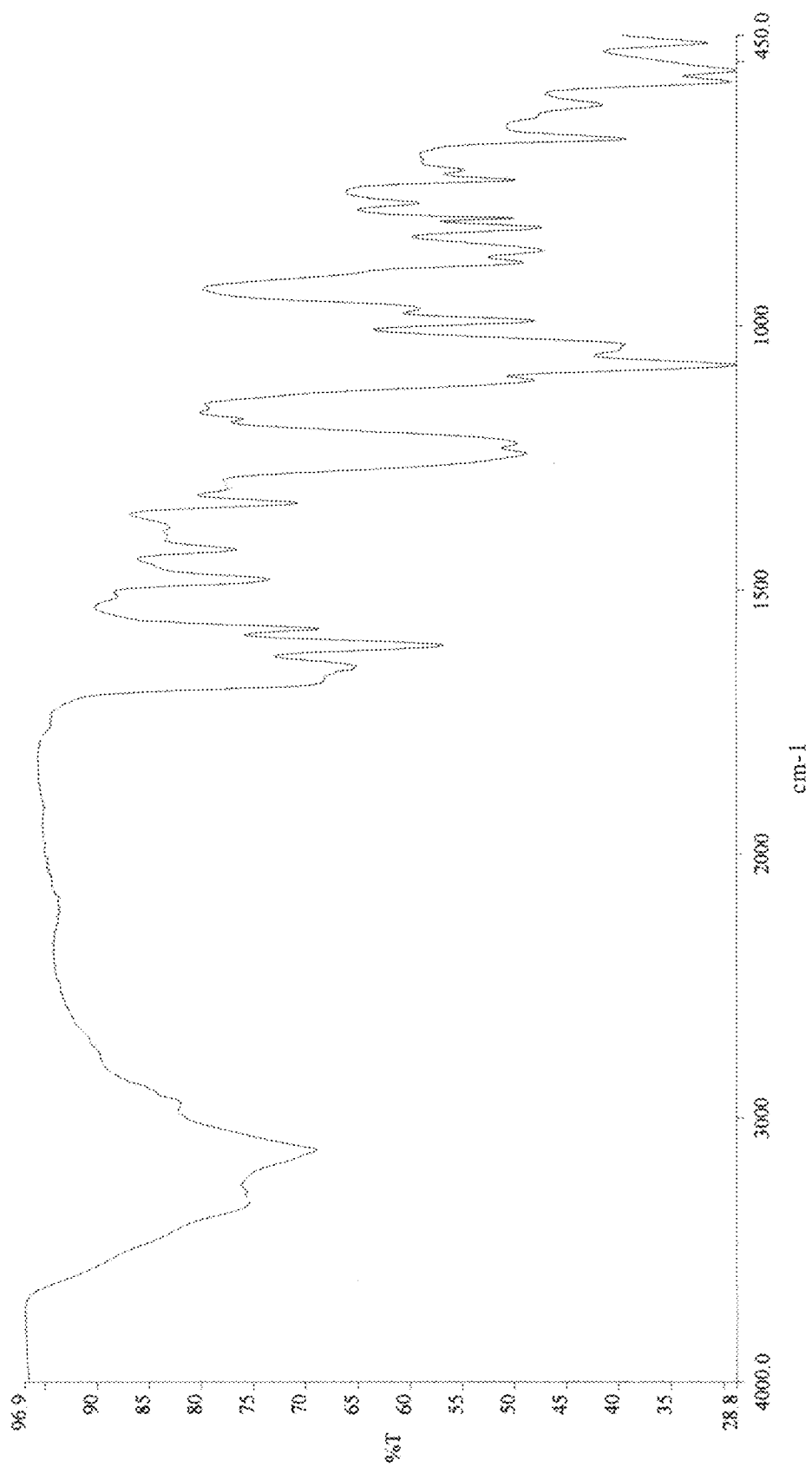
FIG. 11 shows an infrared absorption spectrum of a freeze-dried product of sodium salt of 3',5'-cyclic diadenylic acid.
Figure 12:
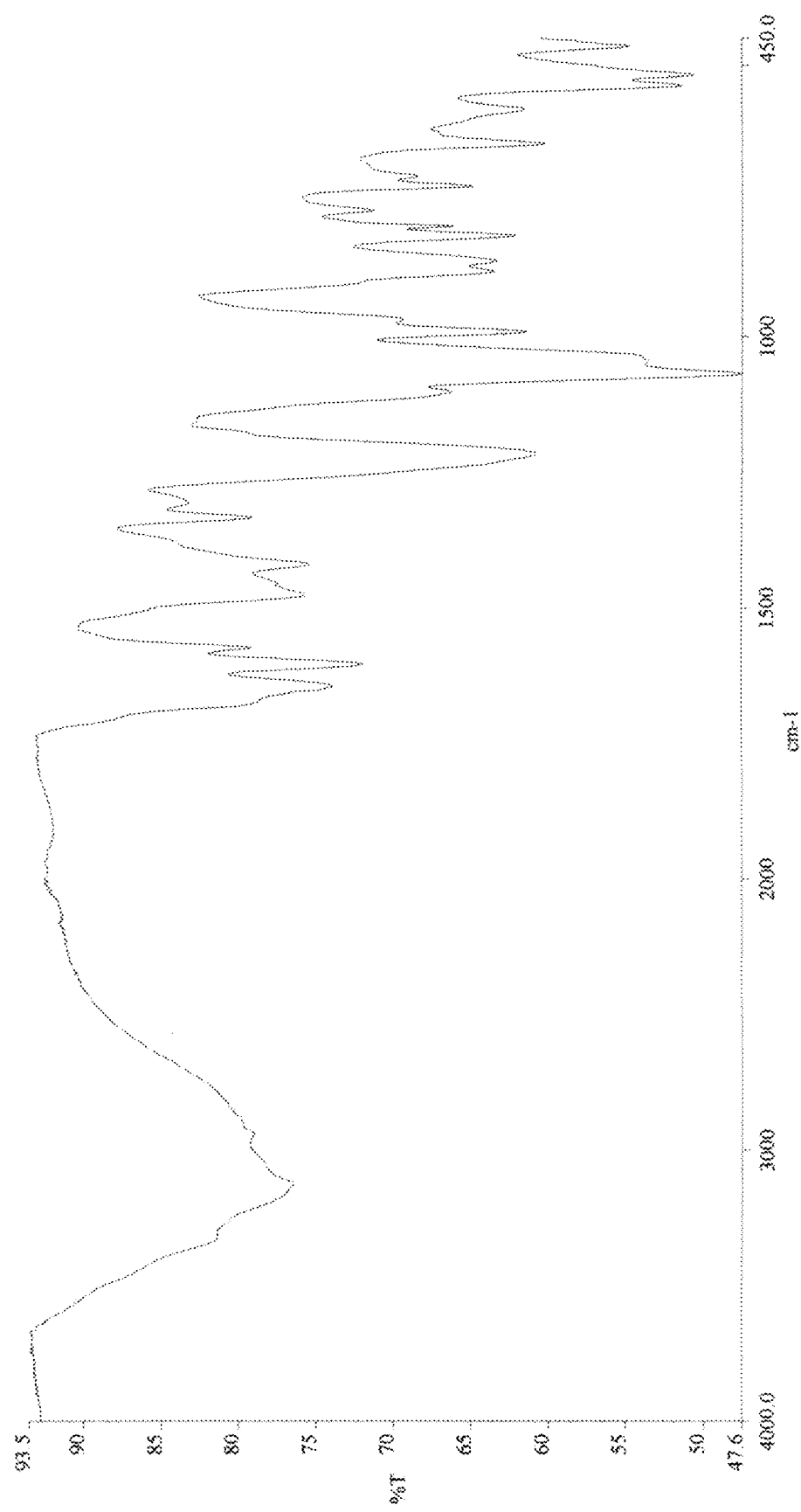
FIG. 12 shows an infrared absorption spectrum of a freeze-dried product of ammonium salt of 3',5'-cyclic diadenylic acid.

The values of characteristic peaks (cm$^{-1}$) observed for each of the inclusion compounds and freeze-dried products are shown in Table 1. Further, infrared absorption spectra of the inclusion compound of 3',5'-cyclic diadenylic acid of the present invention, the freeze-dried product of sodium salt of 3',5'-cyclic diadenylic acid, and the freeze-dried product of ammonium salt of 3',5'-cyclic diadenylic acid are shown in FIGS. 10 to 12, respectively.

As a result, the inclusion compound of 3',5'-cyclic diadenylic acid of the present invention had characteristic peaks around 3087, 1686, 1604, 1504, 1473, 1415, 1328 and 1213 (cm$^{-1}$).

TABLE 1

| Inclusion Compound (cm$^{-1}$) | Freeze-Dried Product of Sodium Salt (cm$^{-1}$) | Freeze-Dried Product of Ammonium Salt (cm$^{-1}$) |
| --- | --- | --- |
| 3087 | 3131 | 3104 |
| 1686 | 1647 | 1644 |
| 1604 | 1605 | 1604 |
| 1504 | 1574 | 1573 |
| 1473 | 1481 | 1475 |
| 1415 | 1423 | 1420 |
| 1328 | 1335 | 1333 |
| 1213 | 1234 | 1219 |
|  | 1103 |  |

(F) X-Ray Powder Diffractometry

An X-ray diffraction spectrum of the inclusion compound of 3',5'-cyclic diadenylic acid of the present invention was measured under the following measurement condition.

(Measurement Condition)
Target: Cu
X-ray tube current: 40 mA
X-ray tube voltage: 45 kV
Scan range: 2θ=4.0 to 40.0°
Pretreatment: Pulverization using an agate mortar As a result of the measurement, no apparent peaks were observed in the pattern of the X-ray diffraction spectrum, revealing that said inclusion compound was amorphous.

Example 3

[1] Manufacture of Inclusion Compound of 3',5'-Cyclic Diadenylic Acid (1)

3',5'-Cyclic diadenylic acid was synthesized enzymatically by a known method, and purification was performed. A solution (280 mL) of 3',5'-cyclic diadenylic acid obtained by purification, with OD257 of 473, was diluted with water such that OD257 became 40. 2 N hydrochloric acid was added with stirring so as to adjust pH to 1.8. As a result, white solids precipitated in the aqueous solution.

In order to obtain the inclusion compound more efficiently, said solution was warmed to 50° C. using a programmable incubator. Thereafter, the solution was cooled with a temperature gradient of −3° C./hr until the temperature of the solution reached 4° C. causing solids to precipitate. Precipitates were collected by a glass filter (17G3) to obtain white solids. Said white solids were vacuum dried at a room temperature and the inclusion compound of 3',5'-cyclic diadenylic acid was obtained.

[2] Manufacture of Inclusion Compound of 3',5'-Cyclic Diadenylic Acid (2)

3',5'-Cyclic diadenylic acid was synthesized enzymatically by a known method, and purification was performed. A solution (400 mL) of 3',5'-cyclic diadenylic acid obtained by purification, with OD257 of 758, was diluted with water such that OD257 became 100. In order to obtain the inclusion compound more efficiently, said solution was warmed to 50° C. using a programmable incubator, and 2 N hydrochloric acid was added with stirring so as to adjust pH to 1.8.

Then the solution was cooled with a temperature gradient of −4° C./hr until the temperature of the solution reached 4° C. causing solids to precipitate. Precipitates were collected by a glass filter (17G3) to obtain white solids. Said white solids were vacuum dried at a room temperature and 8.5 g of the inclusion compound of 3',5'-cyclic diadenylic acid was obtained.

Figure 13:
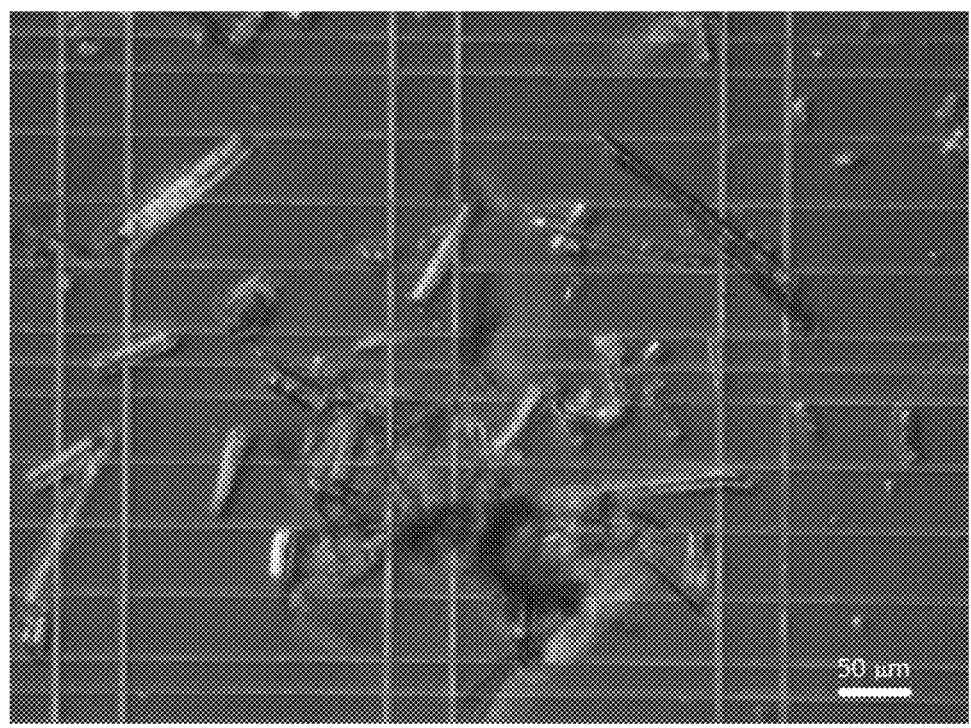
FIG. 13 shows a photograph of an inclusion compound (crystalline) of 3',5'-cyclic diadenylic acid.

(Example 4) Physical Properties of Inclusion Compound (Crystalline) of 3',5'-Cyclic Diadenylic Acid (H) Shape A photograph of the inclusion compound (crystalline) of 3',5'-cyclic diadenylic acid prepared in Example 3 above is shown in FIG. 13. As seen from FIG. 13, the inclusion compound (crystalline) of 3',5'-cyclic diadenylic acid was needle-shaped.

(I) Differential Scanning Calorimetry

Figure 14:
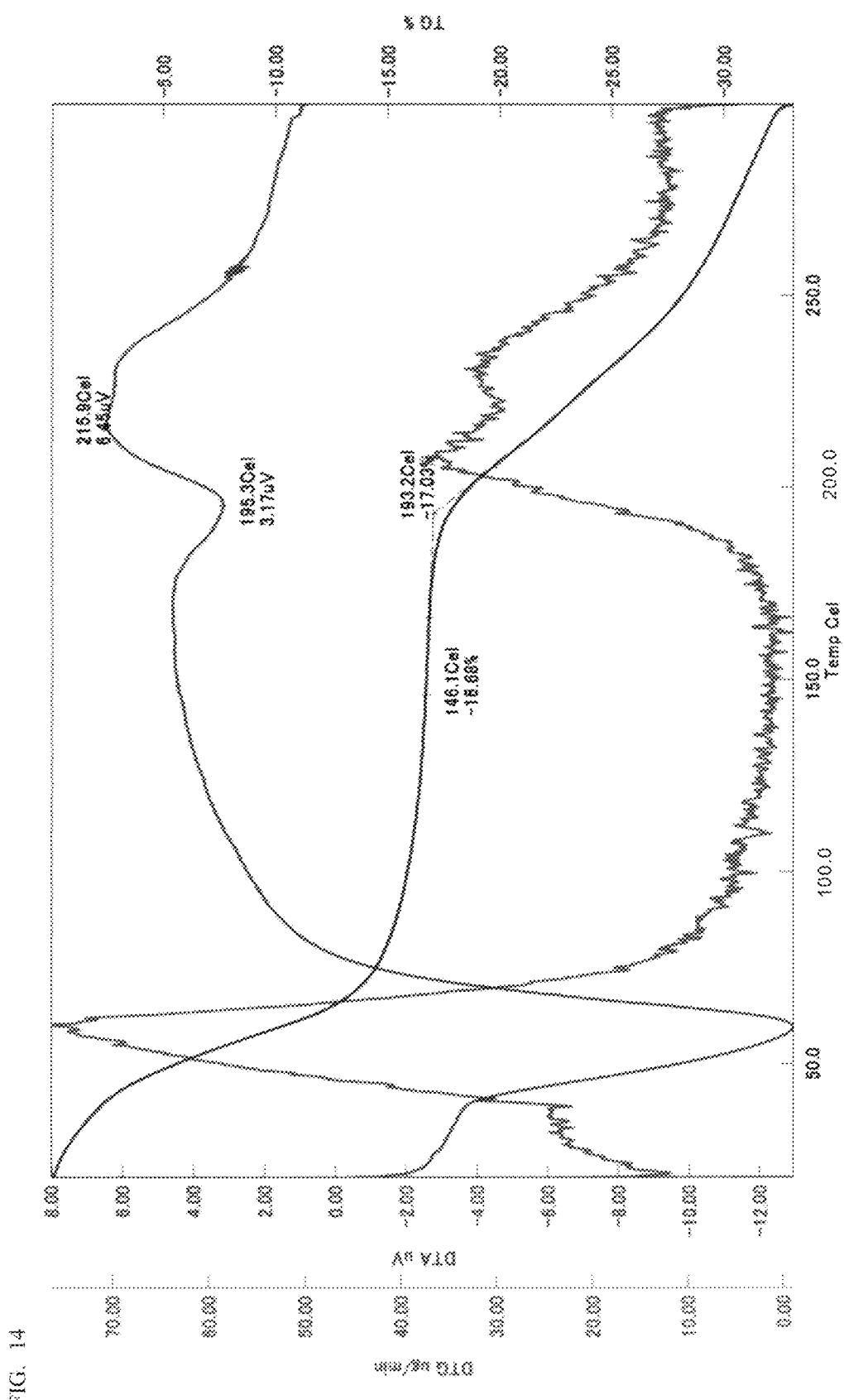
FIG. 14 shows a result of thermogravimetric measurement/differential thermal analysis of an inclusion compound (crystalline) of 3',5'-cyclic diadenylic acid.

When analyzed by a thermogravimetric measurement/differential thermal analysis (TG/DTA) apparatus (temperature elevation rate of 5° C./min), the inclusion compound of 3',5'-cyclic diadenylic acid of the present invention showed a characteristic endothermic peak around 193° C. (FIG. 14).

(J) Water Content

When analyzed by a thermogravimetric measurement/differential thermal analysis (TG/DTA) apparatus (temperature elevation rate of 5° C./min), water content of the inclusion compound of 3',5'-cyclic diadenylic acid of the present invention was 17.0% after removing water by vacuum drying under the condition of a temperature of 20° C. for 2 hours.

(K) X-Ray Powder Diffractometry

An X-ray diffraction spectrum was measured on the inclusion compound of 3',5'-cyclic diadenylic acid of the present invention under the same measurement condition as in (G).

Figure 15:
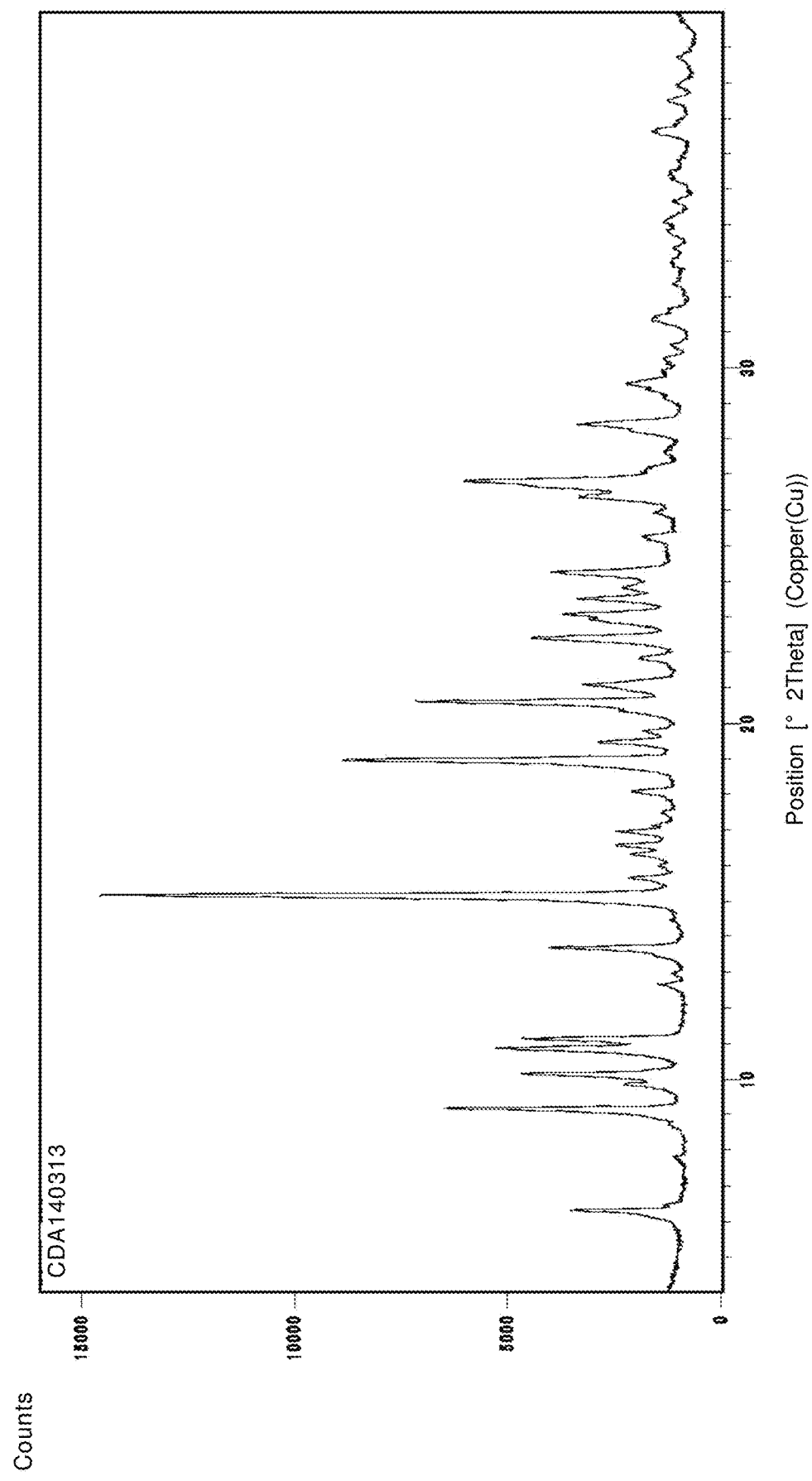
FIG. 15 shows an X-ray diffraction spectrum of an inclusion compound (crystalline) of 3',5'-cyclic diadenylic acid.

As a result, as shown in FIG. 15 and Table 2, the inclusion compound of 3',5'-cyclic diadenylic acid of the present invention showed characteristic peaks around 9.2, 10.2, 10.9, 11.1, 13.7, 15.2, 19.0, 20.6, 22.4, 23.1, 24.3, 26.6 and 26.8 (°) in diffraction angle (2θ).

Further, from the pattern of the X-ray diffraction spectrum, it was found that the inclusion compound of 3',5'-cyclic diadenylic acid obtained in this Example is a crystalline substance.

TABLE 2

| 2θ (°) | Relative Intensity (%) |
|---|---|
| 9.2 | 41.9 |
| 10.2 | 28.5 |
| 10.9 | 32.1 |
| 11.1 | 27.9 |
| 13.7 | 23.5 |
| 15.2 | 100 |
| 19.0 | 59.2 |
| 20.6 | 46.4 |
| 22.4 | 26.8 |
| 23.1 | 21.7 |
| 24.3 | 23.5 |
| 26.6 | 25.6 |
| 26.8 | 38.9 |

(L) Purity Test

Purity of the inclusion compound (crystalline) of 3',5'-cyclic diadenylic acid was analyzed by the high performance liquid chromatography method. As a result, purity of 3',5'-cyclic diadenylic acid was 99.7%. Note that the condition of the high performance liquid chromatography method was the same as that in Example 1.

What is claimed is:

1. A crystal of 3',5'-cyclic diadenylic acid, wherein the crystal has water content of 3.5 to 17% as measured by a thermogravimetric measurement/differential thermal analysis (TG/DTA) apparatus.

2. The crystal of 3',5'-cyclic diadenylic acid of claim 1, having purity of 97% or more as measured by high-performance liquid chromatography.

3. The crystal of 3',5'-cyclic diadenylic acid of claim 1, having purity of 99% or more as measured by high-performance liquid chromatography.

4. The crystal of 3',5'-cyclic diadenylic acid of claim 1, wherein the crystal shows characteristic peaks around 9.2±0.45, 15.2±0.75, 19.0±0.94, 20.6±1.02 and 26.8±1.33) (°) in diffraction angle (2θ) in X-ray powder analysis.

* * * * *